United States Patent [19]
Ravenscroft

[11] Patent Number: 6,156,055
[45] Date of Patent: Dec. 5, 2000

[54] GRIPPING DEVICE FOR IMPLANTING, REPOSITIONING OR EXTRACTING AN OBJECT WITHIN A BODY VESSEL

[75] Inventor: Adrian C. Ravenscroft, Milton, Mass.

[73] Assignee: Nitinol Medical Technologies Inc., Boston, Mass.

[21] Appl. No.: 09/274,108

[22] Filed: Mar. 23, 1999

[51] Int. Cl.[7] .................................................. A61B 17/28
[52] U.S. Cl. ............................................ 606/206; 606/127
[58] Field of Search ..................................... 606/127, 205, 606/206

[56] References Cited

U.S. PATENT DOCUMENTS

| | | | |
|---|---|---|---|
| 5,176,687 | 1/1993 | Hasson et al. | 606/127 X |
| 5,312,417 | 5/1994 | Wilk | 606/127 X |
| 5,370,647 | 12/1994 | Graber et al. | 606/127 |
| 5,370,657 | 12/1994 | Irie . | |
| 5,464,408 | 11/1995 | Duc . | |
| 5,667,525 | 9/1997 | Ishibashi | 606/206 |
| 5,669,933 | 9/1997 | Simon et al. . | |

*Primary Examiner*—Jeffrey A. Smith
*Attorney, Agent, or Firm*—Nixon Peabody LLP; Daniel W. Sixbey

[57] ABSTRACT

A gripping device operative within a body vessel which includes an elongate, flexible support body having a plurality of spaced gripping members attached to the support body to extend axially outwardly from the outer end thereof. The gripping members are formed to have an expansion position where they angle laterally from the support body. A cone shaped flexible liner forming an open ended enclosure in the expansion position of the gripping members has an outer end connected to the distal ends of the gripping members and an inner end connected to the support body. The flexible liner is surrounded by the gripping members.

25 Claims, 2 Drawing Sheets

GRIPPING DEVICE FOR IMPLANTING, REPOSITIONING OR EXTRACTING AN OBJECT WITHIN A BODY VESSEL

BACKGROUND OF THE INVENTION

Modern medical technology has produced a number of medical devices which are designed for compression into a small size to facilitate introduction into a vascular passageway and which are subsequently expandable into contact with the walls of the passageway. Among these devices are blood clot filters such as the filters shown by U.S. Pat. No. 4,425,908 to Simon. The Simon filter is a permanent filter which, when once implanted is designed to remain in place. However, recoverable filters have also been developed as disclosed by U.S. Pat. No. 5,370,657 to Irie and U.S. Pat. No. 5,669,933 to Simon et al.

In the past, generally a hook type device has been employed to implant and position the prior art filters within a body vessel, and to engage the removable filters to effect the recovery thereof. The problem with a hook type recovery device is that the filter or other implanted artifact which is either being positioned for implantation or recovered is permitted to pivot about the hook and become misaligned. Once the device is misaligned within a body vessel, recovery is extremely difficult and realignment can often not be achieved without complete removal and subsequent reimplantation. There is also a possibility that damage to a vessel wall can occur from a use of a hook type recovery unit.

In an attempt to improve on prior art transluminal implantation and removal units, gripping devices have been devised which include a plurality of loop type gripping members made integral with a central tube and which extend outwardly at an angle to the central tube. These gripping members are adapted to surround a unit to be implanted or extracted, and an axially displaceable sleeve which surrounds the central tube engages and causes the gripping members to move inwardly. Devices of this type, which are shown by U.S. Pat. No. 5,464,408 to Duc, operate effectively when the artifact to be gripped is a relatively large unit, such as a stent, having an extensive outer surface which can be engaged by the loop type gripping members. However, if the device to be gripped is a shaft or a shaft with a knob which may be attached to a filter, the device can become misaligned and the shaft will move through the loops which form the gripping members.

SUMMARY OF THE INVENTION

It is a primary object of the present invention to provide a novel and improved gripping device which is operative within a body vessel for implanting, repositioning, or extracting an object within the vessel.

Another object of the present invention is to provide a novel and improved gripping device having a plurality of elongate, spaced, gripping members attached to a support body which are movable between an expansion position and a contracted position. A flexible liner forming an open ended enclosure in the expansion position of the gripping members is connected to expand and contract with the gripping members to prevent the passage of an object between the gripping members.

A further object of the present invention is to provide a gripping device having an elongate, flexible support body with a plurality of spaced, wire loop gripping members combined with elongate hook members attached to the support body to extend axially outwardly from the outer end thereof. A cone shaped flexible liner forming an open ended enclosure is secured to the outer ends of the gripping members and to the support body and extends internally within the gripping members to center a device being gripped.

A still further object of the present invention is to provide a novel and improved gripping device which includes an elongate flexible central tube and an axially movable outer tube surrounding the central tube. The central tube has an outer end which is formed with a projecting end section of reduced diameter relative to the diameter of the remainder of the central tube and a plurality of spaced gripping and hook members are secured to the central tube around the periphery of the projecting end section. A flexible liner forming an open ended enclosure in an expansion position of the hook and gripping members is attached to the outermost ends of the gripping members and is attached to the projecting end section of the central tube. This liner angles outwardly from the projecting end section internally of the hook and gripping members at a first angle, and then extends to the outermost ends of the hook and gripping members at a second, lesser angle which is substantially equal to the angle at which the hook and gripping members extend from the central tube in the expansion position of the hook and gripping members.

DETAILED DESCRIPTION OF THE PREFERRED EMBODIMENTS

Figure 1:
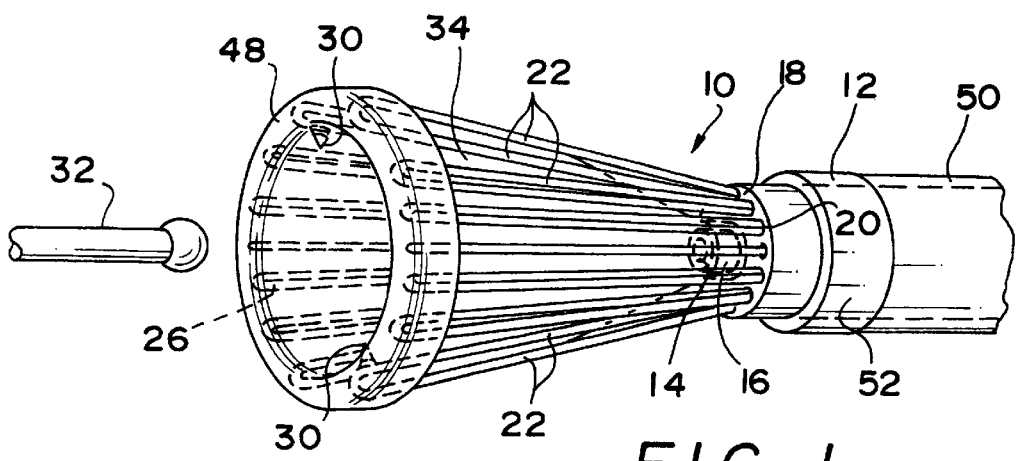
FIG. 1 is a perspective view of the gripping device of the present invention.

Referring now to the drawings, the gripping device of the present invention indicated generally at 10 includes an elongate, flexible support body 12 which is preferably an elongate, flexible tube having a central channel 14 extending therethrough. The channel 14 is adapted to receive a guide wire for guiding a gripping device to a desired location within a body vessel.

The outermost end of the flexible support body 12 is provided with a projecting end section 16 of reduced cross section relative to the remainder of the support body. When the support body is a flexible tube, the diameter of the projecting end section is less than the diameter of the remainder of the central tube to provide a flange 18 at the base of the projecting end section. Extending inwardly from the flange 18 in spaced relationship about the base of the projecting end section 16 are a plurality of lumens 20.

Figure 2:
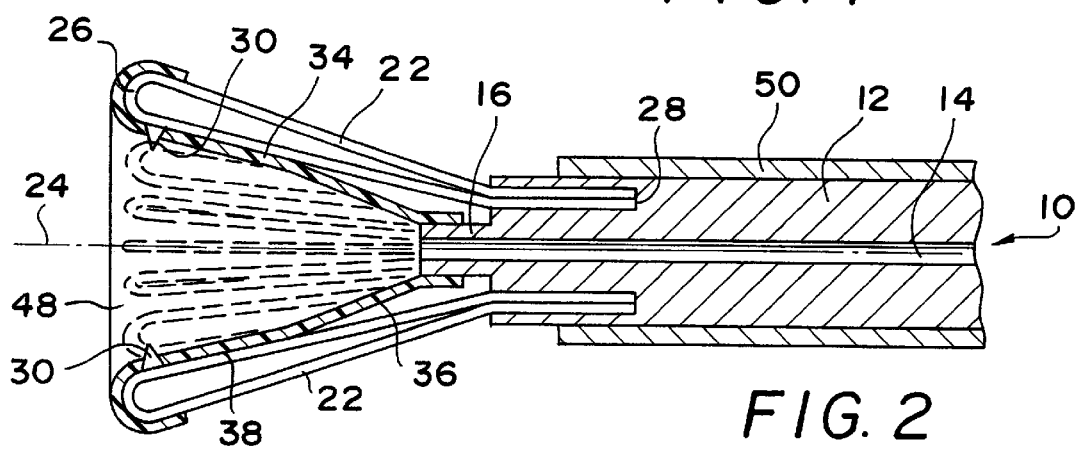
FIG. 2 is a sectional view of the gripping device of FIG. 1.
Figure 3:
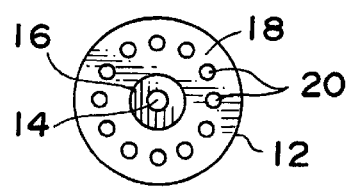
FIG. 3 is a view in end elevation of the central support tube for the gripping device of FIG. 1.
Figure 4:
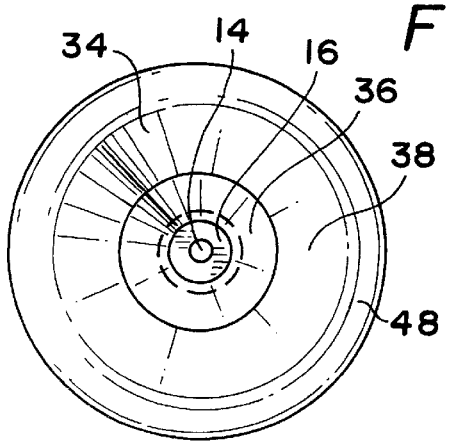
FIG. 4 is a view in end elevation of the gripping device of FIG. 1.

A plurality of spaced gripping members 22 are mounted on the elongate flexible support body 12 to extend axially from the outer end thereof at an angle to the longitudinal axis 24 of the elongate flexible support body. Each gripping member 22 is formed by a length of wire which is looped at 26 to form the distal end of the gripping member. The two free ends of the wire 28 which form the proximal end of the gripping member are then inserted into one of the lumens 20 and are secured within the lumen. The gripping members are formed to surround the projecting end section 16 and are angled outwardly relative to the longitudinal axis 24, preferably at a shallow angle of less than 45°. The wire gripping members are flexible and are formed to assume the expanded position of FIGS. 1 and 2 when they are unrestrained. However, the wire gripping members may be moved inwardly toward the longitudinal axis 24 to a restrained position. At least two diametrically opposed gripping members are provided at their respective distal ends with a projection 30 with extends inwardly toward the longitudinal axis 24.

Figure 5:
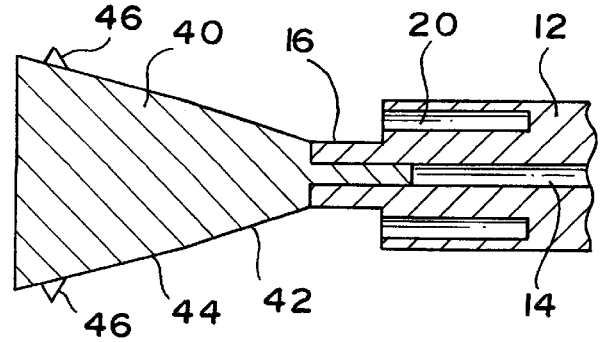
FIG. 5 is a sectional view of the central support tube and a mandrel for forming a liner for the gripping device of FIG. 1.

If the gripping members 22 were alone used in an attempt to grip a shaft 32 attached to a vena cava filter or some other implanted medical device, the shaft would be likely to pass angularly outward from the gripping device 10 between the gripping members 22. The shaft might even become lodged within the loop of one of the gripping members making it difficult to extract a device attached to the shalt and virtually impossible to reposition the device without completely removing the unit from the body vessel. Consequently, it is important to both prevent the shaft from passing between the gripping members and also to center the shaft within the gripping members so that a medical device which has been angularly mispositioned during implantation can be repositioned without being completely removed. To accomplish this, the gripping device 10 is provided with a flexible, open ended liner 34. Preferably, the liner 34 is formed from a polymer such as polyurethane, although the liner could be formed of woven DACRON. As will be noted in FIG. 2, the innermost or closed end of the liner 34 is secured to the projecting end section 16, while the outermost end of the liner is secured to the looped distal ends of the gripping members 22. It is important to note that the liner 34 is unitary but formed in two sections. An innermost section 36 which extends from the projecting end 16 angles outwardly relative to the longitudinal axis 24 at a greater angle than an outermost section of the liner 38. The outermost section of the liner extends at an angle which is substantially equal to the angle at which the gripping members 22 extend relative to the longitudinal axis 24, and thus the outermost section of the liner lies against the gripping members. However, the innermost section 36 of the liner extends at a greater angle relative to the longitudinal axis 24 and is spaced from and gripping members. A liner having this configuration is preferably formed of a polymer, such as a urethane, by dipping on a mandrel 40 shown in FIG. 5. The mandrel 40 is removably mounted in the central channel 14 of the support body 12, and is a circular, cone shaped mandrel having an innermost section 42 formed to the angle of the innermost section 36 of the liner 34 and an outermost section 44 formed to the angle of the outermost section 38 of the liner. With the mandrel in place as shown in FIG. 5, it and the projecting end section 16 are dipped in a molten polymer to form by the dipping process a thin, flexible liner 34. The outer end of the mandrel may be provided with projections 46 to provide apertures in the liner which receive the projections 30 on the gripping members 22. Now the wire gripping members 22 are inserted into the lumens 20 and affixed therein so that the gripping members extend along the outer surface of the liner. With the gripping members in place about the liner, the ends thereof are then again dipped in the molten polymer to create a polymer layer 48 which secures the liner to the distal ends of the gripping members. Once the liner is formed, the mandrel 40 is removed leaving the liner affixed to the projecting end section 16. The flexibility of the liner permits the projections 46 of the mandrel to disengage so that the mandrel can be removed.

To operate the gripping device 10, a flexible catheter 50 or similar flexible outer tubular sheath surrounds the flexible support body 12 and is axially movable along the support body. With the outer tubular body in the position shown in FIGS. 1 and 2, the gripping members 22 are in the expanded position to hold the liner open for the reception of the member such as the shaft 32. As the gripping device is moved over the shaft, the shaft will be centered within the gripping device by contact with the liner 34. The liner will prevent the shaft from passing outwardly between the gripping members 22 and will prevent the shaft from becoming lodged between the gripping members. Once the end of the shaft is in place adjacent to the projecting end section 16, the catheter or outer tubular sheath 50 is moved axially to the left in FIGS. 1 and 2 to engage the gripping members 22 and force them inwardly toward the longitudinal axis 24. Thus the gripping members and the liner will close inwardly about the shaft 32 to grip the shaft so that it and the device to which it is attached may be repositioned or drawn into the tube 50 by retracting the flexible support body 12. It is important to note that the metal gripping members 22 are external to the liner 34 and thus provide hard runner surfaces over which the outer tube 50 can slide without danger of engagement with the liner which might result in damage to the liner. The end of the outer tube 50 may be provided with a reinforced ring 52 to aid in contracting the gripping members 22, and the reinforced ring 52 may be made of metal to provide a radiopaque marker at the end of the outer tube or sheath 50. It is of course important for the projections 30 to have a combined length that is less than the diameter of the sheath 50 so that the complete gripper device can be drawn within the sheath.

Figure 6:
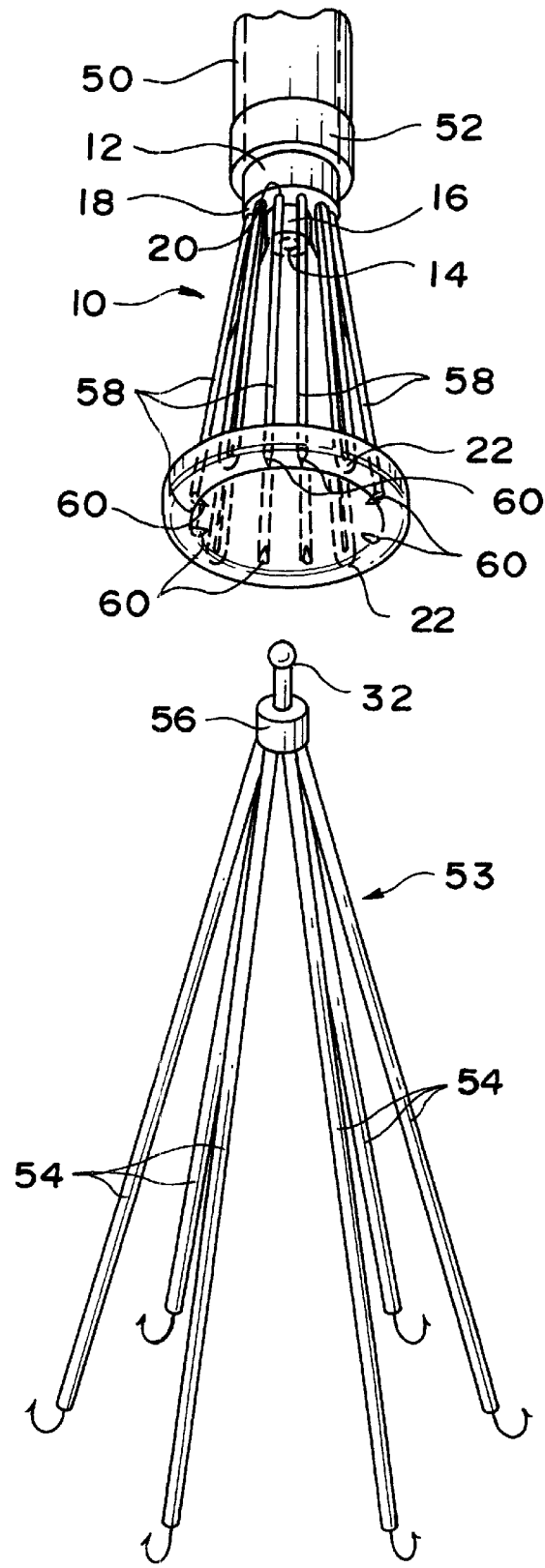
FIG. 6 is a perspective view of a second embodiment of the gripping device of the present invention.

As shown by FIG. 6, it is often desirable to form the gripping device 10 with only three or four loop shaped gripping members 22 which function primarily to expand the flexible open ended liner 34 and to engage and position a filter 53 to be removed. In this case, the filter 53 is a removable filter having a plurality of vessel engaging legs 54 which angle outwardly from a central apex 56 at the shaft 32. With this filter configuration, it is advantageous for the gripping device to positively grip the filter in the area of the apex 56 rather than at the end of the shaft 32. To accomplish this, a plurality of flexible, elongate wire shafts 58 are positioned between the loop shaped gripping members 22. One end of each shaft 58 is secured within a lumen 20, and an inwardly projecting hook 60 is formed at the outermost end 62 of each shaft 58. The shafts 58, like the gripping members 22, extend along the outer surface of the liner 34 and lie against the outermost section 38 of the liner. Like the hooks 30, the hooks 60 project inwardly trough the liner to form a plurality of inwardly projecting hooks spaced around the open end of the liner.

In the operation of the gripping device of FIG. 6, the tubular sheath 50 surrounds the gripping device 10 and holds the device in a collapsed condition adjacent to the longitudinal axis of the device. In this configuration, the gripping device is adapted to travel through a body vessel until it reaches the shaft 32 of the expanded filter 53. Now the sheath 50 is drawn back permitting the gripping members 22, the shafts 58 and the liner 34 to expand outwardly to the configuration shown in FIG. 6. Now the open end of the gripping device is moved over the shaft 32 and beyond the apex 56 of the filter 53 so that the hooks 60 can extend between the filter legs 54. The tubular sheath 50 is moved forwardly over the support body 12 and into engagement with the gripping members 22 and shafts 58 to bring them into engagement with the filter legs 54 below the apex 56. The hooks 60 now pass between the filter legs 54 below the apex while the gripping members 22 and liner 34 extend externally of the filter legs as the gripping members, liner and shafts 58 are moved by the sheath 50 inwardly toward the longitudinal axis of the gripping device. As the support body 12 is drawn into the sheath 50, the hooks positively engage the filter apex 56 to draw the filter into the sheath. The gripping members and liner position the filter so that it is in alignment for withdrawal into the sheath.

Industrial Applicability

The gripping device of the present invention may be employed within a body vessel for implanting, repositioning or extracting a medical device or other object. Since the gripping device operates to center an object which it grips, it may be employed to effectively reposition an angularly mispositioned filter or other medical unit without completely withdrawing the unit from a body vessel. The gripping device is also effective for removing small objects, such as kidney stones, from body vessels since it closes around these objects and prevents them from passing outwardly between the gripping members 22.

I claim:

1. A gripping device operative within a body vessel for implanting, repositioning or extracting an object comprising:
    an elongate support body having a central longitudinal axis and an outer end;
    a plurality of spaced elongate, flexible gripping members substantially circularly arranged and attached to the support body to extend axially outwardly from the outer end thereof, each said gripping member having a proximal end rigidly and nonpivotally secured to said support body and a distal end spaced from the outer end of said support body, said flexible gripping members being formed to angle outwardly from the outer end of said support body and to have an expansion position, when unrestrained, wherein the distal ends thereof are spaced laterally outwardly from said support body and to be flexibly movable, when restrained, inwardly from said expansion position to move said distal ends toward the longitudinal axis of said support body; and
    a flexible liner forming an open ended enclosure in the expansion position of said gripping members, said flexible liner being connected to said gripping members.

2. The gripping device of claim 1 wherein said gripping members include hook members, each of which is formed from an elongate length of flexible material having a hook at the distal end thereof.

3. The gripping device of claim 2 wherein said gripping members include a plurality of loop members each formed from an elongate length of flexible material looped to provide a loop at the distal end thereof and two end sections at the proximal end, said end sections being attached to said support body.

4. The gripping device of claim 3 wherein said flexible liner is formed internally of said gripping members with said gripping members extending externally of said flexible liner.

5. The gripping device of claim 4 wherein said gripping members are formed of metal.

6. The gripping device of claim 5 which includes a restraining unit mounted on said support body in surrounding relationship thereto, said restraining unit being axially displaceable relative to said support body past the outer end thereof to engage said gripping members and move said gripping members toward said longitudinal axis to a restrained position and axially displaceable relative to said support body from engagement with said gripping members in the restrained position inwardly of the outer end of said support body to permit said gripping members to move to the expansion position.

7. The gripping device of claim 6 wherein said support body is an elongate flexible central tube and said restraining unit is an outer tube surrounding said central tube.

8. The gripping device of claim 7 wherein said outer tube has a forward end to engage said gripping members, said forward end being provided with a reinforced ring.

9. The gripping device of claim 8 wherein said reinforced ring is a metal ring.

10. The gripping device of claim 4 wherein said flexible liner has an open end connected to the distal ends of said gripping members and a closed end connected to said central tube.

11. The gripping device of claim 10 wherein the hooks at the distal ends of said hook members extend inwardly through said flexible liner.

12. A gripping device operative within a body vessel for implanting, repositioning or extracting an object comprising:
    an elongate support body having a central longitudinal axis and an outer end;
    a plurality of spaced gripping members attached to said support body to extend axially outwardly from the outer end thereof, each said gripping member having a proximal end secured to said support body and a distal end spaced from the outer end of said support body and being formed to have an expansion position, when unrestrained, wherein the distal end thereof is spaced laterally from said support body and to be movable, when restrained, inwardly from said expansion position toward the longitudinal axis of said support body, said gripping members including a plurality of loop members each formed from a length of wire looped to provide a loop at the distal end and two wire end sections at a proximal end, said wire end sections being attached to said support body; and
    a flexible liner forming an open ended enclosure in the expansion position of said gripping members, said flexible liner being connected to said gripping members.

13. The gripping device of claim 12 wherein said flexible liner is attached to the distal ends of said loop members and to the outer end of said support body.

14. The gripping device of claim 13 wherein said liner is formed internally of said gripping members with said gripping members extending externally of said flexible liner.

15. The gripping device of claim 14 wherein said flexible liner is formed of a polymer.

16. The gripping device of claim 14 wherein said gripping members in the expansion position angle outwardly from proximal to distal ends thereof at a first angle relative to said longitudinal axis, said flexible liner having a first section adjacent to the open end thereof which is inclined relative to said longitudinal axis at an angle substantially equal to said first angle, and a second section extending from said first section to said support body at an angle relative to said longitudinal axis which is greater than said first angle, said gripping members being spaced from said second section.

17. A gripping device operative within a body vessel for implanting, repositioning, or extracting an object comprising:
    an elongate support body having a central longitudinal axis and an outer end; said elongate support body being a flexible tube which is formed at the outer end with a projecting end section of reduced diameter relative to the diameter of the remainder of the flexible tube to form a flange at the base of the reduced diameter end section where the end section meets the remainder of the flexible tube, and a plurality of spaced lumens are formed in said tube to extend longitudinally into the tube from said flange, said lumens being spaced around the base of the reduced diameter end section, a plurality of spaced gripping members attached to said support body to extend axially outwardly from the outer end thereof, each said gripping member having a proximal end secured to said support body with the proximal end of each gripping member being received in a lumen, and a distal end spaced from the outer end of said support body, said gripping members being formed to have an expansion position, when unrestrained, wherein the distal ends thereof are spaced laterally from said support body and to be movable, when restrained, inwardly from said expansion position toward the longitudinal axis of said support body; and a flexible liner connected to said gripping members and forming an open ended enclosure in the expansion position of said gripping members, said flexible liner being formed internally of said gripping members with said gripping members extending externally of said flexible liner.

18. The gripping device of claim 17 wherein said liner is attached to said reduced diameter end section.

19. The gripping device of claim 18 Wherein said gripping members include a plurality of looped members each formed from a length of wire looped to provide a loop at a distal end and two wire end sections at a proximal end, the wire end sections of each looped member being secured respectively in a lumen.

20. The gripping device of claim 19 wherein said gripping members in the expansion position angle outwardly from the proximal to the distal ends thereof at a first angle relative to said longitudinal axis, said flexible liner having a first section adjacent to the open end thereof which is connected to the distal ends of said gripping members and which is inclined relative to said longitudinal axis at an angle substantially equal to said first angle, and a second section extending from said first section to said projecting end section of said flexible tube at an angle relative to said longitudinal axis which is greater than said first angle, said gripping members being spaced from said second section.

21. The gripping device of claim 20 wherein the distal ends of at least two gripping members are positioned to be diametrically opposed, the diametrically opposed distal ends being provided with inwardly extending projections which pass through said liner and project inwardly therefrom.

22. A gripping device operative within a body vessel for implanting, repositioning or extracting an object comprising:

an elongate support body having a central longitudinal axis and an outer end;

a plurality of spaced gripping members attached to said support body to extend axially outwardly from the outer end thereof, said gripping members including hook members, each of which is formed of a length of wire having a hook at a distal end thereof, each said gripping member having a proximal end secured to said support body and a distal end spaced from the outer end of said support body, said gripping members being formed to have an expansion position, when unrestrained wherein the distal ends thereof are spaced laterally from said support body to be movable, when restrained inwardly from said expansion position toward the longitudinal axis of said support body; and a flexible liner forming an open ended enclosure in the expansion position of said gripping members, said flexible liner being connected to said gripping members.

23. The gripping device of claim 22 wherein said support body is formed at the outer end with a projecting end section of reduced diameter relative to the diameter of the remainder of the support body, said closed end of said flexible liner being attached to said projecting end section, the proximal ends of said gripping members being secured to said support body around the periphery of said projecting end section.

24. The gripping device of claim 23 wherein said gripping members in the expansion position angle outwardly from the proximal to the distal ends thereof at a first angle of less than 45° relative to said longitudinal axis, said flexible liner having a first section adjacent to the open end thereof which is connected to the distal ends of said gripping members and which is inclined relative to said longitudinal axis at an angle substantially equal to said first angle, and a second section extending from said first section to said projecting end section of said flexible tube at an angle relative to said longitudinal axis which is greater than said first angle, said gripping members being spaced from said second section.

25. The gripping device of claim 17 wherein said gripping members include a plurality of loop members each formed from a length of wire looped to provide a hoop at a distal end and two wire sections at a proximal end, said wire sections being attached to said support body.

* * * * *